(12) United States Patent
Okamoto et al.

(10) Patent No.: US 12,091,683 B2
(45) Date of Patent: Sep. 17, 2024

(54) METHOD FOR PRODUCING PLATELETS, METHOD FOR PRODUCING PLATELET PRODUCT, AND METHOD FOR PRODUCING BLOOD PRODUCT

(71) Applicant: MEGAKARYON CORPORATION, Kyoto (JP)

(72) Inventors: Haruki Okamoto, Kyoto (JP); Chisato Tokikura, Kyoto (JP); Tomohiro Shigemori, Kyoto (JP)

(73) Assignee: MEGAKARYON CORPORATION, Kyoto (JP)

( * ) Notice: Subject to any disclaimer, the term of this patent is extended or adjusted under 35 U.S.C. 154(b) by 609 days.

(21) Appl. No.: 16/648,540

(22) PCT Filed: Sep. 19, 2018

(86) PCT No.: PCT/JP2018/034666
§ 371 (c)(1),
(2) Date: Mar. 18, 2020

(87) PCT Pub. No.: WO2019/059234
PCT Pub. Date: Mar. 28, 2019

(65) Prior Publication Data
US 2020/0216808 A1    Jul. 9, 2020

(30) Foreign Application Priority Data

Sep. 19, 2017 (JP) .................. 2017-179137

(51) Int. Cl.
*C12N 5/078* (2010.01)
(52) U.S. Cl.
CPC ........ *C12N 5/0644* (2013.01); *C12N 2500/32* (2013.01); *C12N 2506/45* (2013.01)
(58) Field of Classification Search
CPC .............. C12N 5/0644; C12N 2500/32; C12N 2506/45
See application file for complete search history.

(56) References Cited

U.S. PATENT DOCUMENTS

| | | | |
|---|---|---|---|
| 2011/0257021 A1 | 10/2011 | Concari et al. | |
| 2016/0022736 A1 | 1/2016 | Feng et al. | |
| 2018/0282697 A1* | 10/2018 | Hirose | ................ A61K 35/14 |

FOREIGN PATENT DOCUMENTS

| | | |
|---|---|---|
| EP | 2 434 012 | 3/2012 |
| EP | 2 500 418 | 9/2012 |
| EP | 2 708 597 | 3/2014 |
| EP | 2 955 223 | 12/2015 |
| EP | 3 363 443 | 8/2018 |
| WO | 2010/134526 | 11/2010 |
| WO | 2011/034073 | 3/2011 |
| WO | 2012/015914 | 2/2012 |
| WO | 2012/157586 | 11/2012 |
| WO | 2014/123242 | 8/2014 |
| WO | 2017/065280 | 4/2017 |

OTHER PUBLICATIONS

Schemmer et al ("Glycine reduces platelet aggregation," Amino Acids (2013) 44:925-931) (Year: 2013).*
Essex et al ("Redox Control of Platelet Aggregation," Biochemistry 2003, 42, 129-136) (Year: 2003).*
Avanzi et al ("A novel bioreactor and culture method drives high yields of platelets from stem cells," Transfusion vol. 56, Jan. 2016). (Year: 2016).*
Reems, et al., "In Vitro Megakaryocyte Production and Platelet Biogenesis: State of the Art", Transfusion Medicine Reviews, vol. 24, No. 1, Jan. 2010, pp. 33-43.
Extended European Search Report issued in corresponding European Patent Application No. 18859680.3, May 18, 2021, 7 pages.
Takayama et al., "Generation of functional platelets from human embryonic stem cells in vitro via ES-sacs, VEGF-promoted structures that concentrate hematopoietic progenitors", Blood, vol. 111, No. 11, pp. 5298-5306 (2008).
Nakamura et al., "Expandable Megakaryocyte Cell Lines Enable Clinically Applicable Generation of Platelets from Human Induced Pluripotent Stem Cells", Cell Stem Cell, vol. 14, No. 4, pp. 535-548 (2014).
Oguro et al., "Senescence and ageing of stem cells regulated by polycomb complexes", Regenerative Medicine, vol. 6, No. 4, pp. 26-32 (2007)—Abstract.
Gil et al., "Regulation of the INK4b-ARF-INK4a tumour suppressor locus: all for one or one for all", Nature Reviews Molecular Cell Biology, vol. 7, pp. 667-677 (2006)—Abstract only.
Kim et al., "Absence of p16INK4a and truncation of ARF tumor suppressors in chickens", PNAS, vol. 100, No. 1, pp. 211-216 (2003).
Takayama et al., "Transient activation of c-MYC expression is critical for efficient platelet generation from human Induced pluripotent stem cells", J. Exp. Med., vol. 207, No. 13, pp. 2817-2830 (2010).
Kobayashi et al., "Generation of Rat Pancreas in Mouse by Interspecific Blastocyst Injection of Pluripotent Stem Cells", Cell, vol. 142, No. 5, pp. 787-799 (2010).
Iscove's Modified Dulbecco's Medium (IMDM), SIGMA Product Information [online], retrieved on Dec. 4, 2018, 3 pages, URL :<https://www.sigmaaldrich.com/content/demi/sigma-aldrich/docs/Sigma/Formulation/i3390for/pdf>.
Karolczak et al., "The role of thiols in blood platelet activation", Postepy Biologii Komorki, vol. 36, No. 1, pp. 101-120 (2009).
International Search Report issued in International Application No. PCT/JP2018/034666, Dec. 25, 2018, 4 pages.

* cited by examiner

*Primary Examiner* — Valarie E Bertoglio
*Assistant Examiner* — Zanna Maria Beharry
(74) *Attorney, Agent, or Firm* — HSML P.C.

(57) ABSTRACT

The present invention provides a method for producing platelets that can improve at least one of the ability of megakaryocyte to produce platelets and the bioactivity of platelets produced even in high-density culture, for example. The method for producing platelets of the present invention includes a platelet producing step of producing platelets from megakaryocytes, wherein the platelet producing step is performed in the presence of at least one of glycine and cysteine.

20 Claims, 4 Drawing Sheets

METHOD FOR PRODUCING PLATELETS, METHOD FOR PRODUCING PLATELET PRODUCT, AND METHOD FOR PRODUCING BLOOD PRODUCT

TECHNICAL FIELD

The present invention relates to a method for producing platelets, a method for producing a platelet product, and a method for producing a blood product.

BACKGROUND ART

Platelet products are administered to patients who are bleeding due to operations, injuries, or the like, or who are suffering from low levels of platelets, or the like. Currently, platelet products are produced from blood obtained through blood donation. However, due to a change in the population composition, there is a concern that the amount of blood donated will decrease and cause a shortage of platelet products.

Furthermore, if blood donors have infectious diseases involving bacteria or the like, their blood may be contaminated with bacteria, and thus there is a risk of infectious diseases caused by administration of platelet products contaminated with bacteria. Thus, methods for producing platelets in vitro are developed (Non-Patent Literature 1).

CITATION LIST

Non-Patent Literature

Non-Patent Literature 1: Takayama N et.al, "Generation of functional platelets from human embryonic stem cells in vitro via ES-sacs, VEGF-promoted structures that concentrate hematopoietic progenitors.", 2008, Blood, Vol. 111, No.11, pages 5298-5306

SUMMARY OF INVENTION

Technical Problem

For large-scale production of platelets, it is desirable to perform megakaryocyte culture at a high cell density (hereinafter also referred to as "high-density culture") to obtain platelets at a high density. Therefore, the inventors of the present invention have attempted high-density culture. However, it has been found that there is a problem in that the ability of megakaryocyte to produce platelets is decreased or the bioactivity of platelets produced from the megakaryocyte is decreased in the high-density culture.

With the foregoing in mind, it is an object of the present invention to provide a method for producing platelets that can improve at least one of the ability of megakaryocyte to produce platelets and the bioactivity of platelets produced even in high-density culture, for example.

Solution to Problem

In order to achieve the above object, the present invention provides a method for producing platelets including a platelet producing step of producing platelets from megakaryocytes, wherein the platelet producing step is performed in the presence of at least one of glycine and cysteine.

The present invention also provides a method for producing a platelet product, including a product producing step of producing a platelet product from platelets, wherein the platelets are obtained using the method for producing platelets according to the present invention.

The present invention also provides a method for producing a blood product, including a blood product producing step of producing a blood product by mixing platelets and other components, wherein the platelets are obtained using the method for producing platelets according to the present invention.

Advantageous Effects of Invention

The present invention can improve at least one of the ability of megakaryocyte to produce platelets and the bioactivity of platelets produced even in high-density culture, for example.

DESCRIPTION OF EMBODIMENTS

Figure 1A:
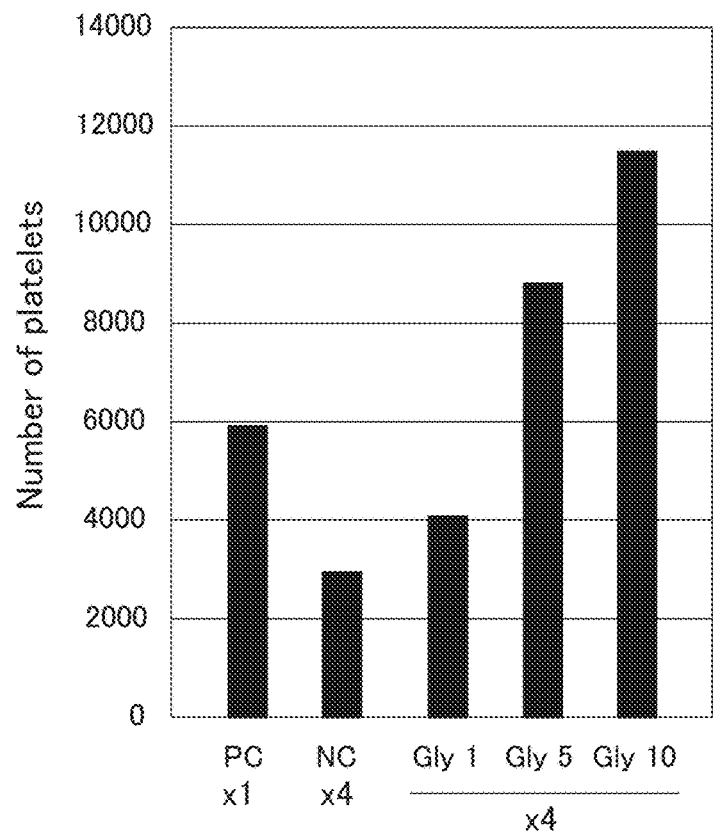
FIGS. 1A and 1B are graphs each showing the number of platelets in Example 1.

In the method for producing platelets of the present invention, the concentration of the glycine is, for example, 2 mmol/L or more. The concentration of the glycine is preferably 6 mmol/L or more and is more preferably 11 to 21 mmol/L or more.

In the method for producing platelets of the present invention, the concentration of the cysteine is, for example, 2 mmol/L or more. The concentration of the cysteine is preferably 2 to 11 mmol/L.

In the method for producing platelets of the present invention, the megakaryocyte cell density at the start of production of the platelets is, for example, $3 \times 10^5$ cells/mL or more.

In the method for producing platelets of the present invention, the megakaryocyte is, for example, an immortalized megakaryocyte.

In the method for producing platelets of the present invention, the megakaryocyte is derived from, for example, pluripotent cells. The pluripotent cell is, for example, an artificial pluripotent stem cell.

In the method for producing platelets of the present invention, the megakaryocyte is, for example, derived from human.

<Method for Producing Platelets>

The method for producing platelets of the present invention includes a platelet producing step (hereinafter, also referred to as "producing step") of producing platelets from megakaryocytes, wherein the platelet producing step is performed in the presence of at least one of glycine and cysteine. The method for producing platelets of the present invention is characterized in that the platelet producing step is performed in the presence of at least one of glycine and cysteine, and other steps and conditions are not particularly limited. Regarding the method for producing platelets of the present invention, for example, reference can be made to the descriptions as to the method for producing a platelet product, the method for producing a blood product, the platelet product, and the blood product of the present invention described below.

As a result of intensive studies, the inventors of the present invention have found that the ability of megakaryocyte to produce platelets can be improved by performing the high-density culture in the presence of glycine. In addition, it was estimated that the ability of megakaryocyte to produce platelets is improved when glycine activates a glycine receptor expressed in the megakaryocyte and chloride ion ($Cl^-$) flows into the megakaryocyte. The estimation does not limit the present invention by any means. Furthermore, as a result of intensive studies, the inventors of the present invention have found that the bioactivity platelets produced can be improved by performing the high-density culture in the presence of cysteine, although the mechanism is unknown. Thus, according to the present invention, for example, at least one of the ability of megakaryocyte to produce platelets and the bioactivity of platelets produced can be improved even in the high-density culture, so that at least one of the efficient (high yield) production of platelets and the production of highly functional platelets can be achieved in the high-density culture.

In the present invention, a "megakaryocyte" is the largest cell in bone marrow in a living body, and means a cell that releases platelets or functions in an equivalent manner. The cell that functions in an equivalent manner means a cell that can produce platelets. In the present invention, a megakaryocyte may be a megakaryocyte before multinucleation (polyploidization), that is, an immature megakaryocyte or a megakaryocyte in the growth phase, or a megakaryocyte after multinucleation (multinucleated megakaryocyte). Specific examples of the megakaryocyte include a promegakaryoblast, a megakaryoblast, a promegakaryocyte, and a mature megakaryocyte. It is sufficient that the number of sets of chromosomes included in the megakaryocyte after multinucleation is more than two, and is specifically 16 to 32, for example.

There is no particular limitation on the source from which the megakaryocytes are derived, and examples thereof include human and non-human animals. Examples of the non-human animals include primates such as monkeys, gorillas, chimpanzees, and marmosets, mice, rats, dogs, cats, rabbits, sheep, horses, and guinea pigs.

In the present invention, the megakaryocytes can be specified by a cell surface marker. If megakaryocytes are human derived, the cell surface marker may be CD41a, CD42a, and CD42b. That is to say, the megakaryocytes are cells that are positive for CD41a, CD42a, and CD42b. If megakaryocytes are human derived, the cell surface marker may be, for example, at least one selected from the group consisting of CD9, CD61, CD62p, CD42c, CD42d, CD49f, CD51, CD110, CD123, CD131, and CD203c.

The ability of megakaryocyte to produce platelets can be represented, for example, by a ratio (P/M ratio) of the number of platelets (P) after the platelet producing step to the number of megakaryocytes (M) at the start of production of platelets. The suppression of the decrease of the ability of megakaryocyte to produce platelets or the improvement of the ability of megakaryocyte to produce platelets means that the P/M ratio is significantly higher than the P/M ratio at the time of performing the high-density culture in the absence of glycine and cysteine, for example.

In the present invention, a "platelet" is one of the cell components in blood, and is a cell component that is positive for CD41a and CD42b. A platelet does not have, for example, a cell nucleus, and, furthermore, is smaller than a megakaryocyte. Therefore, a platelet and a megakaryocyte can be distinguished from each other, for example, according to whether or not there is a cell nucleus and/or the size. It is known that a platelet plays an important role in forming a blood clot and stopping bleeding, and relates to regeneration of damaged tissues and physiological processes of inflammation. Furthermore, it is known that, when platelets are activated through bleeding or the like, receptors of cell integrins such as Integrin αIIBβ3 (glycoprotein IIb/IIIa; a complex of CD41a and CD61) are expressed on membranes of the platelets. Furthermore, when platelets are activated, the platelets aggregate and fibrin coagulates due to various blood coagulation factors released from the platelets, and thus blood clots are formed to facilitate stop of bleeding. In the present invention, the source from which the platelets are derived is the same as the source from which the megakaryocytes are derived.

In the present invention, the bioactivity of platelets can be evaluated using a known method. The bioactivity of platelets can be evaluated as the amount of activated platelets, for example, using an antibody for PAC-1 that specifically binds to Integrin αIIBβ3 on membranes of activated platelets. Furthermore, the bioactivity of platelets may also be evaluated as the amount of activated platelets, for example, by detecting CD62p (P-selectin), which is a platelet activation marker, using an antibody. The bioactivity of platelets may also be evaluated, for example, through flow cytometry, by performing gating using an antibody for an activation-independent platelet marker CD61 or CD41, and then detecting the binding of an anti-PAC-1 antibody or an anti-CD62p antibody. The bioactivity of platelets may also be evaluated in the presence of adenosine diphosphate (ADP).

In the present invention, the bioactivity of platelets may be evaluated, for example, based on whether or not the platelets bind to fibrinogen in the presence of ADP. When platelets bind to fibrinogen, integrin that is necessary in the early stage of formation of a blood clot is activated. Moreover, the bioactivity of platelets may be observed, for example, by visualizing formation of a blood clot in vivo as shown in FIG. 6 of WO 2011/034073.

In the present invention, for example, "highly functional (high bioactivity)" means that the bioactivity of platelets measured by any of the aforementioned methods is significantly higher or tends to be higher than platelets obtained by conventional methods, i.e., platelets produced in the absence of glycine and cysteine; or that the bioactivity of platelets measured by any of the aforementioned methods is equivalent to the bioactivity of platelets isolated from the organism. The "highly functional" may also mean, for example, that the bioactivity of platelets measured by any of the aforementioned methods is 50% or more, 60% or more, 70% or more, 80% or more, or 90% or more compared with the bioactivity of platelets isolated from the organism.

For example, if platelets have a low CD42b expression percentage or a low Annexin V positive rate, the platelets can be evaluated as having deteriorated or being abnormal (hereinafter, these states may be collectively referred to as "deterioration"), that is, the bioactivity of platelets can be evaluated as being low. Thus, the lower the percentage of deteriorated platelets in platelets produced, the higher the bioactivity of platelets produced, for example. Platelets that have deteriorated do not have, for example, a sufficient function of forming a blood clot (blood coagulating function) or stopping bleeding, and thus the clinical usefulness thereof is low.

In the present invention, the "deterioration of platelets" means a decrease in CD42b (GPIbα) on the platelet surface. That is, deteriorated platelets include, for example, platelets in which the CD42b expression has been lowered, and platelets in which the extracellular region of CD42b has been cleaved through a shedding reaction. When CD42b is no more present on the platelet surface, the platelets cannot associate with von Willebrand factors (VWFs), and thus the blood coagulating function of platelets is lost. The deterioration of platelets can be evaluated using, as an indicator, the CD42b negative rate (or the number of CD42b negative particles) to the CD42b positive rate (or the number of CD42b positive particles) in the platelet fractions. Specifically, it can be evaluated that the higher the CD42b negative rate to the CD42b positive rate is or the larger the number of CD42b negative particles to the number of CD42b positive particles is, the more the platelets are deteriorated. The CD42b positive rate means the percentage of platelets to which anti-CD42b antibodies can bind among the platelets contained in the platelet fractions. The CD42b negative rate means the percentage of platelets to which anti-CD42b antibodies cannot bind among the platelets contained in the platelet fractions.

In the present invention, for example, an "abnormal platelet" is referred to as a platelet in which phosphatidylserine, which is a negatively charged phospholipid, is exposed to the outside from the inside of the lipid bilayer. It is known that, in a living body, phosphatidylserines become exposed on the surface in accordance with activation of platelets, and many blood coagulation factors bind thereto, and thus blood coagulation cascade is amplified. Meanwhile, in abnormal platelets, for example, many phosphatidylserines are always exposed on the surface, and thus, if abnormal platelets are administered to a patient, excessive blood coagulation occurs, which may result in a serious pathological condition such as disseminated intravascular coagulation, for example. Furthermore, since it is known that Annexin V binds to phosphatidylserines, phosphatidylserines on the platelet surface can be detected, for example, using a flow cytometer using, as an indicator, the binding amount of fluorescence-labeled Annexin V. Therefore, the amount of the abnormal platelets can be evaluated by the Annexin V positive rate in the platelet fractions, that is, the percentage or the number of platelets to which Annexin binds. Specifically, it can be evaluated that the higher the Annexin V positive rate or larger the number of Annexin V particles, the more the abnormal platelets in the target platelets.

In the method for producing platelets of the present invention, the platelet producing step (hereinafter also referred to as "producing step") produces platelets from megakaryocytes, as described above. The producing step can be performed, for example, by culturing the megakaryocytes in the presence of a medium. The megakaryocytes may be cultured, for example, on feeder cells, or without feeder cells. The megakaryocytes can be cultured, for example, through float culturing, and thus they can be cultured without feeder cells. The "feeder cells" means cells that are co-cultured with the target cells in order to prepare an environment necessary for culturing cells (target cells) to be proliferated or differentiated. The feeder cells may be cells distinguishable from the target cells, and may be cells derived from the same species as the target cells, or may be cells derived from different species from the target cells. The feeder cells may be, for example, cells that have been treated so as not to proliferate by antibiotics, anticancer agents, gamma irradiation, and the like.

The megakaryocytes can be induced from, for example, cells that are more undifferentiated than megakaryocytes. Therefore, the method for producing platelets of the present invention may include, for example, in advance of the producing step, a megakaryocyte inducing step of inducing megakaryocytes from cells that are more undifferentiated than the megakaryocytes. Regarding the medium, culture condition, and the like in the megakaryocyte inducing step, reference can be made to the description as to the producing step described below.

The "cells that are more undifferentiated than megakaryocytes" means cells having a potential to be differentiated into megakaryocytes. Specifically, for example, the cells that are more undifferentiated than megakaryocytes are, for example, hematopoietic stem cells, hematopoietic progenitors, CD34 positive cells, megakaryocyte-erythroid progenitors (MEP), megakaryocyte progenitors, and the like. The cells that are more undifferentiated than megakaryocytes may be isolated from, for example, bone marrow, cord blood, peripheral blood, or the like, or may be induced from pluripotent cells such as embryonic stem cells (ES cell), induced pluripotent stem cells (iPS cells), nuclear transfer ES cells (ntES cells), germinal stem cells, somatic stem cells, embryonal carcinoma cells, or the like.

There is no particular limitation on the method for inducing megakaryocytes, and known inducing methods may be used. Specifically, the method for inducing megakaryocytes may be, for example, described in WO 2011/034073, WO 2012/157586, or the like. Specifically, for example, in the megakaryocyte inducing step, for example, an oncogene and a polycomb gene may be forcibly expressed in the cells that are more undifferentiated than megakaryocytes. Accordingly, in the megakaryocyte inducing step, for example, immortalized megakaryocytes that infinitely proliferate can be obtained. Moreover, for example, if the forced expression in the immortalized megakaryocytes is canceled, the immortalized megakaryocytes can be induced to multinucleated megakaryocytes, and platelets can be produced. Furthermore, in the megakaryocyte inducing step, for example, an apoptosis suppressor may be forcibly expressed in the megakaryocyte progenitors. Accordingly, in the megakaryocyte inducing step, the immortalized megakaryocytes can be obtained. Moreover, for example, if the forced expression in the immortalized megakaryocytes is canceled in the producing step described below, multinucleated megakaryocytes can be induced from the immortalized megakaryocytes, and platelets can be produced.

In the megakaryocyte inducing step, for example, the oncogene, the polycomb gene, and the apoptosis suppressor may be forcibly expressed. In this case, the oncogene, the polycomb gene, and the apoptosis suppressor may be forcibly expressed simultaneously or at different times. Specifically, for example, in the megakaryocyte inducing step, a procedure may be employed in which, after the oncogene and the polycomb gene are forcibly expressed, the forced expression is canceled, and then the apoptosis suppressor are forcibly expressed, in which the oncogene, the polycomb gene, and the apoptosis suppressor are forcibly expressed, or in which the oncogene and the polycomb gene are forcibly expressed, and the apoptosis suppressor is expressed. Accordingly, in the megakaryocyte inducing step, the immortalized megakaryocytes can be obtained. Moreover, for example, if the forced expression in the immortalized megakaryocytes is canceled in the producing step described below, multinucleated megakaryocytes can be induced from the immortalized megakaryocytes, and platelets can be produced.

In order to improve the efficiency in introducing the genes, for example, the megakaryocyte inducing step preferably includes a first expressing step of forcibly expressing an oncogene and a polycomb gene in cells that are more undifferentiated than megakaryocytes, a second expressing step of forcibly expressing an apoptosis suppressor such as a Bcl-xL gene in the undifferentiated cells, and a canceling step of canceling all the forced expressions. As described above, by canceling the forced expression, for example, multinucleated megakaryocytes can be induced from the immortalized megakaryocytes, and platelets can be produced. Therefore, the canceling step may be referred to as the producing step.

The genes can be forcibly expressed and the forced expression can be canceled, for example, using known methods such as the methods described in WO 2011/034073, WO 2012/157586, WO 2014/123242, or Reference Document 1 below, or equivalent methods. Specifically, for example, the genes can be forcibly expressed and the forced expression can be canceled, for example, using a drug-responsive gene expression inducing system. Examples of the gene expression inducing system include a Tet-on (registered trademark) system, a Tet-off (registered trademark) system, and the like. When the Tet-on system is used, for example, in the forcibly expressing step, culturing is performed in the presence of a drug that induces gene expression, such as tetracycline or doxycycline, and, in the step of canceling the forced expressions, the culturing is performed in the absence of the drug.

Reference Document 1: Nakamura S et al, "Expandable megakaryocyte cell lines enable clinically applicable generation of platelets from human induced pluripotent stem cells.", Cell Stem Cell, 2014, vol.14, No.4, pages 535-548

In the present invention, the "oncogene" means a gene that can induce carcinogenesis of cells in a living body, and examples thereof include MYC family genes such as c-MYC, N-MYC, and L-MYC, SRC family genes, RAS family genes, RAF family genes, protein kinase family genes such as c-kit (CD117), PDGFR (platelet growth factor receptor), and Abl (Abelson murine leukemia viral oncogene homolog), and the like.

In the present invention, the "polycomb gene" means a gene that is known to function to negatively control CDKN2a (cyclin-dependent kinase inhibitor 2A, INK4a/ARF), thereby avoiding cellular aging (Reference Documents 2 to 4 below). Specific examples of the polycomb gene include BMI1 (Polycomb complex protein BMI-1, polycomb group RING finger protein 4 (PCGF4), RING finger protein 51 (RNF51)), Mel18 (Polycomb group RING finger protein 2), Ring (Ring Finger Protein) 1a/b, Phc (Polyhomeotic Homolog) 1/2/3, Cbx (Chromobox) 2/4/6/7/8, Ezh2 (Enhancer Of Zeste 2 Polycomb Repressive Complex 2 Subunit), Eed (Embryonic Ectoderm Development), Suz12 (SUZ12 Polycomb Repressive Complex 2 Subunit), HADC (Histone deacetylases), Dnmt (DNA (cytosine-5)-methyltransferase)1/3a/3b, and the like.

Reference Document 2: Hideyuki Oguro et al, "Senescence and Ageing of Stem Cells Regulated by Polycomb Complexes", Regenerative Medicine, 2007, vol.6, No.4, pages 26-32

Reference Document 3: Jesus Gil et.al, "Regulation of the INK4b-ARF-INK4a tumour suppressor locus: all for one or one for all", Nature Reviews Molecular Cell Biology, 2007, vol.7, pages 667-677

Reference Document 4: Soo-Hyun Kim et.al., "Absence of p16$^{INK4a}$ and truncation of ARF tumor suppressors in chickens", PNAS, 2003, vol.100, No.1, pages 211-216

In the present invention, the "apoptosis suppressor" means a gene having a function that can suppress cellular apoptosis, and examples thereof include BCL2 (B-cell lymphoma 2), Bcl-xL (B-cell lymphoma-extra large), Survivin (Baculoviral IAP Repeat Containing 5), MCL1 (BCL2 Family Apoptosis Regulator), and the like.

The producing step is then performed in the presence of at least one of glycine and cysteine as described above. Specifically, the producing step produces platelets from megakaryocytes in the presence of a medium containing at least one of glycine and cysteine, for example. The producing step may be performed, for example, in the presence of glycine or cysteine, or may be performed in the presence of glycine and cysteine. The producing step can be performed, for example, by replacing the medium containing megakaryocytes with a medium containing at least one of glycine and cysteine, or by adding at least one of glycine and cysteine to the medium containing megakaryocytes.

Glycine and cysteine may, for example, be derivatives thereof. The derivatives are not particularly limited, and examples thereof include isomers or salts thereof, solvates or hydrates thereof, and the like. The isomer may be, for example, an optical isomer or the like.

In the producing step, the concentration of the glycine is not particularly limited, and the concentration of the glycine may be within a range that exhibits an effect of improving the the ability to produce platelets. The lower limit of the concentration of the glycine is not particularly limited, and the concentration of the glycine is, for example, 2 mmol/L, and is preferably 6 mmol/L or 11 mmol/L in view of obtaining highly functional platelets. The upper limit of the concentration of the glycine is not particularly limited, and is, for example, 41 mmol/L, 40 mmol/L, 31 mmol/L, 30 mmol/L, 21 mmol/L, or 20 mmol/L. The range of the concentration of glycine is, for example, 2 to 41 mmol/L or 2 to 40 mmol/L, and is more preferably 6 to 31 mmol/L, 6 to 30 mmol/L, 11 to 31 mmol/L, 11 to 30 mmol/L, 11 to 21 mmol/L, or 11 to 20 mmol/L in view of further improving the ability to produce platelets and obtaining particularly functional platelets. When the producing step is performed in the presence of the medium containing glycine, the concentration of the glycine is the concentration of the glycine contained in the medium at the time of addition of glycine to the medium or replacement with the medium containing glycine. Therefore, when glycine is added to the medium, the concentration of the glycine means the concentration of the glycine in the medium after being added with glycine. When the medium is replaced with a medium containing glycine, the concentration of the glycine means the concentration of the glycine in the medium replaced.

In the producing step, the concentration of the cysteine is not particularly limited, and the concentration of the cysteine may be within a range that exhibits an effect of improving the ability to produce platelets. The lower limit of the concentration of the cysteine is not particularly limited, and the concentration of the cysteine is, for example, 2 mmol/L. The upper limit of the concentration of the cysteine is not particularly limited, and is, for example, 11 mmol/L or 10 mmol/L. The range of the concentration of the cysteine is preferably 2 to 11 mmol/L or 2 to 10 mmol/L, for example, in view of obtaining particularly functional platelets.

The methods for measuring the concentration of the glycine and the concentration of the cysteine may be known methods, and specific examples thereof include a measurement method using a high performance liquid chromatograph (HPLC), a liquid chromatography-mass spectrometry, and the like.

The period of producing platelets from megakaryocytes in the producing step is not particularly limited, and is, for example, 1 to 10 days or 3 to 6 days. In the producing step, the period of culturing in the presence of at least one of glycine and cysteine is not particularly limited, and can be appropriately determined depending on, for example, the number of platelets produced, bioactivity of platelets produced, and the like. The glycine and cysteine are present, for example, during all or part of the producing step.

When the megakaryocyte is induced by forced expression of at least one selected from the group consisting of the oncogene, the polycomb gene, and the apoptosis-suppressing gene, as described above, the megakaryocyte produces the platelet by cancelling the forced expression. Therefore, the production can be performed by replacing the medium containing megakaryocyte with, for example, a medium containing at least one of glycine and cysteine, or by adding at least one of glycine and cysteine to the medium containing megakaryocyte at the time of or after the cancellation of the forced expression. The addition of or replacement with at least one of glycine and cysteine may be performed, for example, once or twice or more.

The producing step may be performed in the presence of an aryl hydrocarbon receptor (AhR) inhibitor, for example, in view of improving bioactivity of platelets produced. Specifically, the producing step is performed, for example, in the presence of a medium containing an AhR inhibitor. The producing step can be performed by replacing the medium containing megakaryocyte with, for example, a medium containing an AhR inhibitor, or by adding an AhR inhibitor to the medium containing megakaryocyte, for example.

The AhR is a transfer factor belonging to Per/ARNT/SIM (PAS) family. The AhR, for example, is inactive in the ligand-free state and migrates into the nucleus when an aromatic hydrocarbon compound binds as a ligand. Then, after the intranuclear migration, the AhR forms a heterodimer with, for example, an Ahr nuclear translocator (ARNT), and combines with an xenobiotic responsive element (XRE) (also referred to as DRE) to activate the transcription.

The AhR inhibitor is not particularly limited, and may be, for example, an AhR antagonist, an expression suppressing nucleic acid molecule capable of suppressing the expression of AhR, or the like. The AhR antagonist is not particularly limited and examples thereof include 4-(2-(2-(Benzo[b]thiophen-3-yl)-9-isopropyl-9H-purin-6-ylamino)ethyl)phenol (SR1), α-naphthoflavone (CAS 604-59-1), 1,4-dihydrocyanthraquinone, 1,5-dihydrocyanthraquinone, 1,8-dihydrocyanthraquinone, galangin (CAS 548-83-4), resveratrol, 2-methyl-2H-pyrazole-3-carboxylic acid (2-methyl-4-o-tolylazo-phenyl)-amide (CH-223191), N-(2-(3H-Indol-3-yl)ethyl)-9-isopropyl-2-(5-methyl-3-pyridyl)-7H-purin-6-amine (GNF351), 2-(29-amino-39-methoxyphenyl)-oxanaphthalen-4-one (PD98059), (Z)-3-[(2,4-dimethylpyrrol-5-yl)methylidenyl]-2-indolinone (TSU-16), 6,2',4'-trimethoxyflavone (TMF), 3',4'-dimethoxyflavone (DMF), and the like. The AhR antagonist may also be, for example, a compound described as an AhR antagonist in WO 2012/015914.

The period of culturing in the presence of the AhR inhibitor is not particularly limited, and can be appropriately determined depending on, for example, the number of platelets produced, the bioactivity of platelets produced, and the like. The AhR inhibitor is present, for example, during all or part of the producing step. When the AhR inhibitor is added to the medium after the cancellation of the forced expression, for example, the release of functional platelets is started about 3 days after the addition of the AhR inhibitor, and the number of functional platelets increases as the number of culture days increases. When the AhR-inhibitor is SR1, the culture period is preferably about 5 days in view of obtaining particularly functional platelets.

In the producing step, the concentration of the AhR inhibitor is not particularly limited, and can be appropriately determined depending on the type of compound and its effective concentration. The concentration of the AhR antagonist can, for example, as follows in view of further improving the bioactivity of platelets produced.

SR1: 200 nmmol/L or more and less than 1000 mmol/L
CH-223191: 0.2 μmol/L or more and less than 4 μmol/L
GNF351: 20 nmol/L or more and less than 300 nmol/L
TMF: 2.5 μmol/L or more and less than 40 μmol/L
DMF: 2.5 μmol/L or more and less than 40 μmol/L When the megakaryocyte is induced by forced expression of at least one selected from the group consisting of the oncogene, the polycomb gene, and the apoptosis-suppressing gene, the producing step can be performed, for example, by replacing the medium containing megakaryocyte with the medium containing the AhR inhibitor, or by adding the AhR inhibitor to the medium containing megakaryocyte at the time of or after the cancellation of the forced expression. When the AhR inhibitor is added after the cancellation of the forced expression, the AhR inhibitor is preferably added within 1, 2, or 3 days after the cancellation of the forced expression, for example, in the producing step. The addition of or replacement with the AhR inhibitor may be performed, for example, once or twice or more.

The producing step may be performed in the presence of a ROCK inhibitor, for example, in view of improving the bioactivity of platelets produced. Specifically, the producing step is performed, for example, in the presence of a medium containing a ROCK inhibitor. In the producing step, for example, the ROCK inhibitor and the AhR inhibitor are preferably used in combination in view of obtaining highly functional platelets. The producing step can be performed by replacing the medium containing megakaryocyte with, for example, a medium containing a ROCK inhibitor, or by adding a ROCK inhibitor to the medium containing megakaryocyte, for example. When the ROCK inhibitor and the AhR inhibitor are used in combination, the ROCK inhibitor and the AhR inhibitor may be added or replaced at the same time, or may be added or replaced separately, for example.

The ROCK means Rho-associated coiled-coil forming kinase (ROCK). The ROCK inhibitor may be, for example, a ROCK antagonist, an expression suppressing nucleic acid molecule capable of suppressing the expression of ROCK, or the like. Examples of the ROCK inhibitor include (R)-(+)-trans-N-(4-pyridyl)-4-(1-aminoethyl)-cyclohexanecarboxamide (Y-27632), 4-[(1R)-1-aminoethyl]-N-(1H-pyrrolo[2,3-b]pyridin-4-yl)benzamide (Y-39983), fasudil salt (Fasudil(HA1077) hydrochloride), 4-fluoro-5-[[(2S)-hexahydro-2-methyl-1H-1,4-diazepin-1-yl]sulfonyl]-isoquinoline (Ripasudil), 2-(3-(4-((1H-indazol-5-yl)amino)quinazolin-2-yl)phenoxy)-N-isopropylacetamide (SLx-2119), N-[(3-Hydroxyphenyl)methyl]-N'-[4-(4-pyridinyl)-2-thiazolyl]urea dihydrochloride (RKI-1447), 6-Chloro-N4-[3,5-difluoro-4-[(3-methyl-1H-pyrrolo[2,3-b]pyridin-4-yl)oxy]phenyl]-2,4-pyrimidinediamine (TC-S 7001, Azaindole 1), N-[2-[2-(Dimethylamino)ethoxy]-4-(1H-pyrazol-4-yl)phenyl-2,3-dihydro-1,4-benzodioxin-2-carboxamide (SR-3677), Staurosporine, (S)-(+)-2-Methyl-1-[(4-methyl-5-isoquinolinyl)sulfonyl]homopiperazine (H-1152), rac-(2R)-2-(dimethylamino)-N-(1-oxo-1,2-dihydroisoquinolin-6-yl)-2-(thiophen-3-yl)acetamide (AR-12286), N-(1-{[4-(methylsulfanyl)phenyl]methyl}piperidin-3-yl)-1H-indazol-5-amine (INS-117548), and the like. In the producing step, the concentration of the ROCK inhibitor is not particularly limited, and can be appropriately determined depending on the type of compound and its effective concentration.

When the megakaryocyte is induced by forced expression of at least one selected from the group consisting of the oncogene, the polycomb gene, and the apoptosis-suppressing gene, the producing step can be performed, for example, by replacing the medium containing megakaryocyte with the medium containing the ROCK inhibitor, or by adding the ROCK inhibitor to the medium containing megakaryocyte at the time of or after the cancellation of the forced expression. When the ROCK inhibitor is added after the cancellation of the forced expression, the ROCK inhibitor is preferably added within 1, 2, or 3 days after the cancellation of the forced expression, for example, in the producing step. The addition of or replacement with the AhR inhibitor may be performed, for example, once or twice or more.

In the producing step, the megakaryocyte cell density at the start of production of platelets is not particularly limited. The lower limit of the megakaryocyte cell density is, for example, $1 \times 10^5$ cells/mL, $2 \times 10^5$ cells/mL, $3 \times 10^5$ cells/mL, or $4 \times 10^5$ cells/mL. The upper limit of the megakaryocyte cell density is not particularly limited, and is, for example, $4 \times 10^5$ cell/mL, $6 \times 10^5$ cell/mL, or $8 \times 10^5$ cell/mL. The range of the cell density is, for example, $1 \times 10^5$ cells/mL to $8 \times 10^5$ cells/mL, $2 \times 10^5$ cells/mL to $8 \times 10^5$ cells/mL, $3 \times 10^5$ cells/mL to $6 \times 10^5$ cells/mL, or $4 \times 10^5$ cells/mL to $6 \times 10^5$ cells/mL. The cell density can be calculated, for example, by dividing the number of megakaryocyte cells by the volume of the medium in which megakaryocyte is suspended.

In the producing step, there is no particular limitation on the culturing conditions of the megakaryocytes, and ordinary culturing conditions of the megakaryocytes may be adopted. Specifically, for example, the culturing temperature is, for example, about 35 to about 42° C., about 36 to about 40° C., or about 37 to about 39° C. The $CO_2$ concentration is, for example, about 5 to about 15%. The $O_2$ concentration is, for example, about 15 to about 25%, or about 20%.

There is no particular limitation on the medium, and examples thereof include known media suited to produce platelets from the megakaryocytes, and equivalent media. Specifically, for example, the medium can be prepared, for example, using, as a basal medium, a medium that is used to culture animal cells. Examples of the basal medium include single media such as an IMDM medium, a Medium 199 medium, an Eagle's Minimum Essential Medium (EMEM) medium, an αMEM medium, a Dulbecco's modified Eagle's Medium (DMEM), a Ham's F12 medium, an RPMI1640 medium, a Fischer's medium, and a Neurobasal (registered trademark) Medium (manufactured by Thermo Fisher Scientific), and mixed media thereof. The medium may contain, for example, serum or plasma, or may be a non-serum medium without containing them. The source from which the serum and plasma are derived is preferably the same as the source from which the megakaryocytes are derived. Specifically, for example, if the megakaryocytes are human derived, both the serum and the plasma are preferably human derived.

The medium may contain, for example, other components. There is no particular limitation on the other components, and examples thereof include albumin, insulin, transferrin, selenium, fatty acid, microelements, 2-mercaptoethanol, thiolglycerol, monothioglycerol (MTG), lipid, amino acid (e.g., L-glutamine), ascorbic acid, heparin, non-essential amino acid, vitamins, growth factor, low molecular weight compound, antibiotic, antioxidant, pyruvic acid, buffer, inorganic salts, cytokine, and the like. These other components may be contained, for example, alone or in combination of two or more. The cytokine is, for example, a substance that facilitates differentiation of blood cells, and specific examples thereof include a vascular endothelial growth factor (VEGF), thrombopoietin (TPO), various TPO-like agonists, a stem cell factor (SCF), an ITS (insulin-transferrin-selenite) supplement, an ADAM inhibitor, an FLT inhibitor, a WNT inhibitor, and the like. It is preferable that the medium is, for example, an IMDM medium containing serum, insulin, transferrin, serine, thiolglycerol, ascorbic acid, and TPO. For example, the medium may further contain SCF, and may further contain heparin. There is no particular limitation on the concentrations of the other components. The concentration of the TPO is, for example, about 10 ng/mL to about 200 ng/mL, or about 50 ng/mL to about 100 ng/mL. The concentration of the SCF is, for example, about 10 ng/mL to about 200 ng/mL, or about 50 ng/mL. The concentration of the heparin is, for example, about 10 U/mL to about 100 U/mL, or about 25 U/mL. The medium may further contain, for example, a phorbol ester (e.g., phorbol-12-myristate-13-acetate; PMA).

In this manner, platelets can be produced from the megakaryocytes. The medium after the producing step contains, for example, the platelets.

The method for producing platelets of the present invention may include, for example, a purification step for purifying platelets obtained in the producing step. The method for purifying platelets is not particularly limited, and can be performed by a known method such as a purification method using a separation unit such as a hollow-fiber membrane, a purification method by centrifugation, or the like.

<Platelets>

The platelets of the present invention are characterized by being obtained using the method for producing platelets of the present invention. The platelets of the present invention are characterized by being obtained using the method for producing platelets of the present invention, and there is no particular limitation on the other steps and conditions. For example, the description of the method for producing platelets of the present invention is applicable to the platelets of the present invention.

<Method for Producing Platelet Product>

As described above, the method for producing a platelet product of the present invention is characterized by including a product producing step of producing a platelet product from platelets, wherein the platelets are obtained using the method for producing platelets of the present invention. The method for producing a platelet product of the present invention is characterized in that the platelets are obtained using the method for producing platelets of the present invention, and there is no particular limitation on the other steps and conditions. The description of the method for producing platelets of the present invention is applicable to the method for producing a platelet product of the present invention.

In the product producing step, for example, other components may be added. Examples of the other components include stabilizers of cells such as platelets, and the like.

The method for producing a platelet product of the present invention may include, before the product producing step, a platelet producing step of producing platelets, using the method for producing platelets of the present invention. For example, the description of the method for producing platelets of the present invention is applicable to the platelet producing step.

<Platelet Product>

The platelet product of the present invention is characterized by being obtained using the method for producing a platelet product of the present invention. The platelet product of the present invention is characterized by being obtained using the method for producing a platelet product of the present invention, and there is no particular limitation on the other steps and conditions. For example, the description of the method for producing platelets of the present invention and the method for producing a platelet product is applicable to the platelet product of the present invention.

<Method for Producing Blood Product>

As described above, the method for producing a blood product of the present invention is characterized by including a blood product producing step of producing a blood product by mixing platelets and other components, wherein the platelets are obtained using the method for producing platelets of the present invention. The method for producing a blood product of the present invention is characterized in that the platelets are obtained using the method for producing platelets of the present invention, and there is no particular limitation on the other steps and conditions. The description of the method for producing platelets of the present invention is applicable to the method for producing a blood product of the present invention.

There is no particular limitation on the other components, and examples thereof include other blood cells such as red blood cells, stabilizers of cells such as platelets, and the like.

The method for producing a blood product of the present invention may include, before the blood product producing step, a platelet producing step of producing platelets, using the method for producing platelets of the present invention. For example, the description of the method for producing platelets of the present invention is applicable to the platelet producing step.

<Blood Product>

The blood product of the present invention is characterized by being obtained using the method for producing a blood product of the present invention. The blood product of the present invention is characterized by being obtained using the method for producing a blood product of the present invention, and there is no particular limitation on the other steps and conditions. For example, the description of the method for producing platelets of the present invention and the method for producing a blood product is applicable to the blood product of the present invention.

<Platelet Productivity Improver>

The platelet productivity improver of the present invention is characterized in that it contains at least one of glycine and cysteine. The platelet productivity improver of the present invention is characterized in that it contains at least one of glycine and cysteine, and other composition and condition are not particularly limited. Regarding the platelet productivity improver of the present invention, for example, reference can be made to the description as to the method for producing platelets of the present invention.

<Platelet Bioactivity Improver>

The platelet bioactivity improver of the present invention is characterized in that it contains at least one of glycine and cysteine. The platelet bioactivity improver of the present invention is characterized in that it contains at least one of glycine and cysteine, and other composition and condition are not particularly limited. Regarding the platelet bioactivity improver of the present invention, for example, reference can be made to the description as to the method for producing platelets of the present invention.

<Use of Glycine or Cysteine>

The present invention relates to the use of at least one of glycines and cysteines to improve the ability to produce platelets. The present invention also relates to the use of at least one of glycine and cysteine for improving the bioactivity of platelets. Regarding the present invention, for example, reference can be made to the description as to the method for producing platelets of the present invention.

EXAMPLES

Hereinafter, the present invention will be described in detail by way of examples, but the present invention is not limited to the aspects described in the examples.

Example 1

The ability of megakaryocyte to produce platelets and the bioactivity of platelets produced are decreased in the high-density culture, and the ability of megakaryocyte to produce platelets and the bioactivity of platelets produced can be improved by performing the high-density culture in the presence of glycine.

(1) Production of Immortalized Megakaryocytes

Immortalized megakaryocytes were produced as follows.

(1-1) Preparation of Hematopoietic Progenitors from iPS Cells

Differentiation culturing was performed to differentiate human iPS cells (TKDN SeV2: human fetal skin fibroblasts-derived iPS cells generated using Sendai virus) to blood cells, using the method described in Reference Document 5 below. Specifically, a human ES/iPS cell colony was co-cultured with C3H10T1/2 feeder cells in the presence of 20 ng/mL of VEGF (manufactured by R&D Systems) for 14 days, so that hematopoietic progenitors (Hematopoietic Progenitor Cells; HPC) were produced. The culturing conditions were 37° C., 20% $O_2$, 5% $CO_2$ (the same conditions were applied below unless otherwise described).

Reference Document 5: Takayama N. et al., "Transient activation of c-MYC expression is critical for efficient platelet generation from human induced pluripotent stem cells", J. Exp. Med., 2010, vo.13, pages 2817-2830

(1-2) Gene Introducing System

As the gene introducing system, a lentiviral vector system was used. A lentiviral vector is a tetracycline-controlled Tet-on (registered trademark) gene expression inducing system vector. It was produced by recombining an mOKS cassette of LV-TRE-mOKS-Ubc-tTA-I2G (Reference Document 6 below) with c-MYC, BMI1 or BCL-xL. The vectors to which c-MYC, BMI1, and BCL-xL were introduced were respectively taken as LV-TRE-c-Myc-Ubc-tTA-I2G, LVTRE-BMI1-Ubc-tTA-I2G, and LV-TRE-BCL-xL-Ubc-tTA-I2G. c-MYC, BMI1, and BCL-xL viruses were produced through gene introduction to 293T cells using the lentiviral vector. Target cells were infected with the obtained viruses, so that c-MYC, BMI1, and BCL-xL genes were introduced to the genomic sequences of the target cells. The genes stably introduced to the genomic sequences can be forcibly expressed by adding doxycycline (clontech #631311) to a medium.

Reference Document 6: Kobayashi, T.et al., "Generation of rat pancreas in mouse by interspecific blastocyst injection of pluripotent stem cells.", Cell, 2010, vol.142, No.5, pages 787-799

(1-3) Infection of Hematopoietic Progenitors with c-MYC and BMI1 Virus

HPC obtained using the method (1-1) was disseminated at $5\times10^4$ cells/well on a 6-well plate on which C3H10T1/2 feeder cells were disseminated in advance, and c-MYC and BMI1 were forcibly expressed using the lentiviral method using BMI1 virus and c-MYC virus. At that time, six wells were used for each type of cell line. Specifically, the virus particles were added to a medium each at an MOI (multiplicity of infection) of 20, and infection was caused through spin infection (32° C., 900 rpm, centrifugation for 60 minutes). The spin infection was performed twice every 12 hours. Human thrombopoietin (TPO) (R&D SYSTEMS), Human Stem Cell Factor (SCF) (R&D SYSTEMS), and Doxycycline (Dox, clontech #631311) were added respectively at concentrations of 50 ng/mL, 50 ng/mL, and 2 µg/mL to a basal medium (IMDM (Iscove's Modified Dulbecco's Medium) (Sigma-Aldrich) containing 15% Fetal Bovine Serum (GIBCO), 1% Penicillin-Streptomycin-Glutamine (GIBCO), 1% Insulin, Transferrin, Selenium Solution (ITS-G) (GIBCO), 0.45 mmol/L 1-Thioglycerol (Sigma-Aldrich), and 50 µg/mL L-Ascorbic Acid (Sigma-Aldrich)) to obtain a medium (hereinafter, referred to as a "differentiation medium"), and protamine was further added thereto to a final concentration of 10 µg/mL to obtain a medium used in the experiments.

(1-4) Production and Maintenance Culturing of Megakaryocytes Self-Propagating Strains While taking the date on which infection with c-MYC and BMI1 virus was caused using the method (1-3) as the $0^{th}$ day of infection, HPC to which c-MYC genes and BMI1 genes were introduced was cultured as follows, and thus megakaryocytes self-propagating strains were produced. Forced expression of c-MYC genes and BMI1 genes was performed by adding DOX to the medium to a concentration of 1 µg/mL.

$2^{nd}$ to $11^{th}$ Days of Infection

On the $2^{nd}$ day of infection, the virus-infected blood cells obtained as described above were collected through pipetting, subjected to centrifugation at 1200 rpm for 5 minutes for removing a supernatant, suspended in a new differentiation medium, and disseminated on new C3H10T1/2 feeder cells (6-well plate). On the $9^{th}$ day of infection, passage was performed by performing a similar operation. In the re-dissemination, the number of cells was counted, and then the cells were disseminated at $1\times10^5$ cells/2 mL/well on C3H10T1/2 feeder cells (6-well plate).

$12^{th}$ to $13^{th}$ Day of Infection

An operation similar to that on the $2^{nd}$ day of infection was performed. After the number of cells was counted, the cells were disseminated at $3\times10^5$ cells/10 mL/100-mm dish on C3H10T1/2 feeder cells (100-mm dish).

$14^{th}$ Day of Infection

The virus-infected blood cells were collected, and were reacted with 2 µL of anti-human CD41a-APC antibody (BioLegend), 1 µL of anti-human CD42b-PE antibody (eBioscience), and 1 µL of anti-human CD235ab-pacific blue (BioLegend) antibody per $1.0\times10^5$ cells. After the reaction, analysis was performed using FACS Verse (trademark) (BD Biosciences). On the $14^{th}$ day of infection, cells with a CD41a positive rate of 50% or more were taken as megakaryocytes self-propagating strains.

(1-5) Infection of Megakaryocytes Self-Propagating Strains with BCL-xL Virus

BCL-xL genes were introduced to the megakaryocytes self-propagating strains on the $14^{th}$ day of infection, using the lentiviral method using BCL-xL virus. The virus particles were added to a medium at an MOI of 10, and infection was caused through spin infection (32° C., 900 rpm, centrifugation for 60 minutes). Forced expression of BCL-xL genes was performed by adding DOX to the medium to a concentration of 1 µg/mL.

(1-6) Production and Maintenance Culturing of Megakaryocyte Immortalized Strains $14^{th}$ to $18^{th}$ Days of Infection Megakaryocytes self-propagating strains to which the BCL-xL genes were introduced, which were obtained using the method (1-5), were collected, and subjected to centrifugation at 1200 rpm for 5 minutes. After the centrifugation, precipitated cells were suspended in a new differentiation medium, and then disseminated at $2\times10^5$ cells/2 mL/well on new C3H10T1/2 feeder cells (6-well plate).

$18^{th}$ Day of Infection: Passage

Megakaryocytes self-propagating strains to which the BCL-xL genes were introduced were collected, the number of cells was counted, and then the cells were disseminated at $3\times10^5$ cells/10 mL/100-mm dish.

$24^{th}$ Day of Infection: Passage

Megakaryocytes self-propagating strains to which the BCL-xL genes were introduced were collected, the number of cells was counted, and then the cells were disseminated at $1\times10^5$ cells/10 mL/100-mm dish. Subsequently, passage was performed in a similar manner every 4 to 7 days, and maintenance culturing was performed. Note that, in the passage, the cells were suspended in a new differentiation medium, and disseminated.

On the $24^{th}$ day of infection, megakaryocytes self-propagating strains to which the BCL-xL genes were introduced were collected, immunostained with 2 µL of anti-human CD41a-APC antibody (BioLegend), 1 µL of anti-human CD42b-PE antibody (eBioscience), and 1 µL of anti-human CD235ab-Pacific Blue (Anti-CD235ab-PB; BioLegend) antibody per $1.0\times10^5$ cells, and then analyzed using FACS Verse (trademark). Then, on the $24^{th}$ day of infection, strains with a CD41a positive rate of 50% or more were taken as immortalized megakaryocyte cell lines. The cells that had proliferated for 24 days or more after infection were taken as immortalized megakaryocyte cell line SeV2-MKCL.

The obtained SeV2-MKCL was subjected to stationary culturing using a 10-cm dish (10 mL/dish). The medium was obtained by adding the components listed below to a basal medium IMDM (concentration means final concentration). The culturing conditions were 27° C., 5% $CO_2$.

FBS (sigma #172012 lot.12E 261) 15%
L-Glutamin (Gibco #25030-081) 2 mmol/L
ITS (Gibco #41400-045) diluted to 100 times
MTG (monothioglycerol, sigma #M6145-25ML) 450 µmol/L
Ascorbic acid (sigma #A4544) 50 µg/mL
Puromycin (sigma #P8833-100MG) 2 µg/mL
SCF (Wako Pure Chemical Industries, Ltd. #193-15513) 50 ng/mL
TPO-like agonists 200 ng/mL (2) Production of Megakaryocyte Culture
(2) Production of Platelets The forced expression was canceled by performing culturing in a medium not containing DOX. Specifically, the immortalized megakaryocyte cell lines (SeV2-MKCL) obtained using the method (1) were washed twice with PBS (−), and suspended in a following platelet producing medium. The cell dissemination density was set to $4.0\times10^5$ cells/mL (×4). Glycine at predetermined concentration (1, 5, or 10, or 10, 20, or 40 mmol/L) was added to each platelet production medium. The platelet production medium contains 0.6 to 0.8 mmol/L of glycine. Therefore, the glycine concentration in the platelet production medium after being added with glycine is about 2 to about 41 mmol/L.

The platelet producing medium was obtained by adding the components listed below to a basal medium IMDM (concentration means final concentration).

FBS 15% or human plasma 5%
L-Glutamin (Gibco #25030-081) 4 mmol/L
ITS (Gibco #41400-045) diluted to 100 times
MTG (monothioglycerol, sigma #M6145-25ML) 450 μmol/L
Ascorbic acid (sigma #A4544) 50 μg/mL
SCF (Wako Pure Chemical Industries, Ltd. #193-15513) 50 ng/mL
TPO-like agonists 200 ng/mL
ADAM inhibitor 15 μmol/L
Aryl hydrocarbon receptor (AhR) Inhibitor (SR1) 750 nmol/L, or GNF351 (Calbiochem #182707) 500 nmol/L
ROCK inhibitor 10 μmol/L or Y39983 (Chemscene LLC #CS-0096) 500 nmol/L
Urokinase 5 U/mL
Heparin 10 U/mL or low molecular heparin (SANOFI, clexane) 1 U/mL The culture was performed for 6 days in the presence of the glycine-added platelet production medium to produce platelets, and the number of platelets produced was counted. As a control, the number of platelets was counted in the same manner except that the cell dissemination density was set to $1.0 \times 10^5$ cells/mL (×1) or $4.0 \times 10^5$ cells/mL (×4) and the glycine-non-added platelet production medium was used. The results thereof are shown in FIGS. 1A and 1B.

Figure 1B:
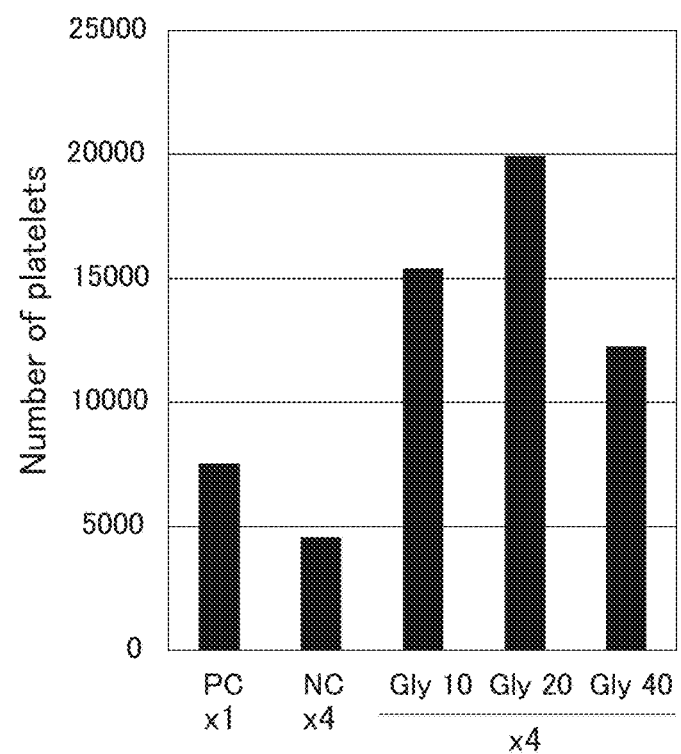

FIGS. 1A and 1B are graphs each showing the number of platelets. FIG. 1A shows the result of the control and the results when the concentrations of added glycine were 1, 5, and 10 mmol/L, and FIG. 1B shows the result of the control and the results when the concentrations of added glycine were 10, 20, and 40 mmol/L. In FIGS. 1A and 1B, the horizontal axis indicates the condition of cell dissemination density and glycine concentration, and the vertical axis indicates the number of platelets. As shown in FIGS. 1A and 1B, when the glycine-non-added platelet production medium was used, the number of platelets obtained in high-density culture ($4.0 \times 10^5$ cells/mL (×4), NC) was reduced by half compared with the culture at a normal megakaryocyte culture density ($1.0 \times 10^5 \times$ cells/mL (×1), PC). That is, the ability of megakaryocyte to produce platelets was reduced to about ⅛. In contrast, when the glycine-added platelet production medium was used, the number of platelets was increased at all concentrations compared with the high-density culture using the glycine-non-added platelet production medium. That is, it has been found that the ability of megakaryocyte to produce platelets in high-density culture can be improved by adding glycine. It has also been found that the ability of megakaryocyte to produce platelets can be further improved when the glycine concentration at the start of production of platelets was 11 to 31 mmol/L or 11 to 21 mmol/L.

(3) Bioactivity of Platelet

The bioactivity of platelets obtained in Example 1(2) was measured using a flow cytometer. Specifically, 900 μL of diluent was added to a 1.5-mL microtube, and 100 μL of culture solution after platelet production was added and mixed. Then, 200 μL of obtained solution was poured into a FACS tube, stained by adding the labeled antibody shown below, and the MFIs of CD62p and PAC-1 in platelets were analyzed using the flow cytometer. The same analysis was also performed using the flow cytometer in NC, and then the increase percentage of the MFIs of CD62p and PAC-1 in the respective samples were calculated with reference to the MFIs of CD62p and PAC-1 in NC. The results thereof are shown in FIGS. 2A and 2B.

Measurement of bioactivity of platelets
0.5 μL anti-CD42a antibody PB label (eBioscience 48-0428-42)
0.5 μL anti-CD42b antibody PE label (Bio Legend 303906)
0.5 μL anti-CD62p antibody APC label (Bio Legend 304910)
10 μL anti-PAC-1 antibody FITC label (BD 303704)

Figure 2A:
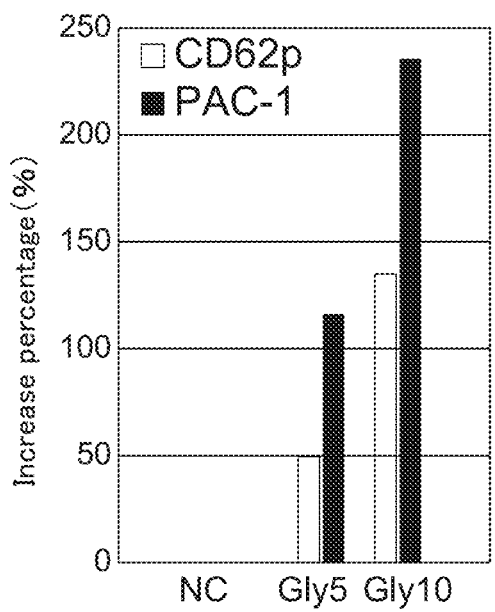
FIGS. 2A and 2B are graphs each showing the increase percentage of MFIs of CD62p and PAC-1 in Example 1.
Figure 2B:
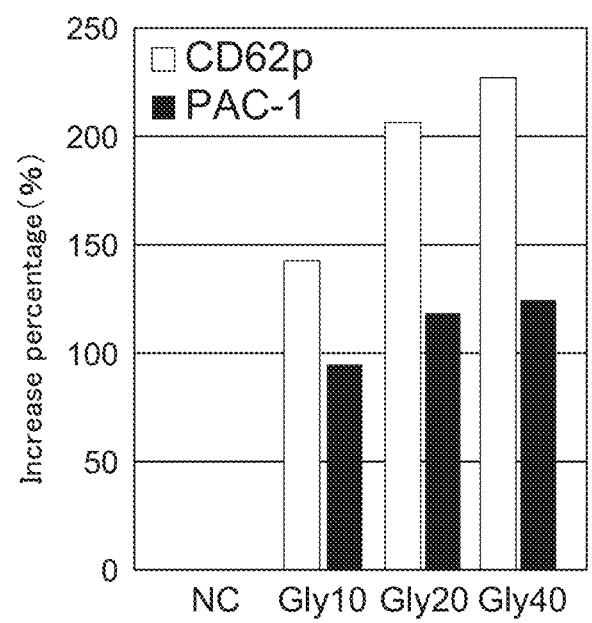

FIGS. 2A and 2B are graphs each showing the increase percentage of MFIs of CD62p and PAC-1. FIG. 2A shows the result of the control and the results when the concentrations of added glycine were 5 and 10 mmol/L, and FIG. 2B shows the result of the control and the results when the concentrations of added glycine were 10, 20, and 40 mmol/L. In FIGS. 2A and 2B, the horizontal axis indicates the condition of cell dissemination density and glycine concentration, and the vertical axis indicates the increase percentage of MFI. As shown in FIGS. 2A and 2B, the expression levels of CD62p and PAC-1 were increased at all glycine concentrations compared to the control without being added with glycine. In addition, the expression levels of CD62p and PAC-1 were increased in a concentration-dependent manner. From these results, it has been found that the bioactivity of platelets produced in high-density culture can be improved by adding glycine.

(4) Platelet Deterioration

Platelets were produced and the number of platelets was counted in the same manner as in Example 1(2) except that the cell dissemination density was set to $1.0 \times 10^5$ cells/mL (×1), $2.0 \times 10^5$ cells/mL (×2), $3.0 \times 10^5$ cells/mL (×3), $4.0 \times 10^5$ cells/mL (×4), or $8.0 \times 10^5$ cells/mL (×8), the platelet production medium containing 0.5 μmol/L GNF-351 was used instead of SR1, and 10 mmol/L glycine and 20 U/mL heparin were added to the platelet production medium. In addition, the deterioration state of platelets obtained was evaluated based on the positive rate of Annexin V. Specifically, in measurement of the Annexin V positive rate in platelets, 100 μL of the culture solution after platelet production was poured into a FACS tube, and the solution was stained by adding the following labeled antibody and protein, diluted to 5 times with an Annexin V binding buffer (BD Biosciences) immediately before flow cytometer analysis, and then subjected to analysis. As a control, the same analysis was performed except that the cell dissemination density was set to $1.0 \times 10^5$ cells/mL (×1), $3.0 \times 10^5$ cells/mL (×3), or $4.0 \times 10^5$ cells/mL (×4) and no glycine or heparins was added. The results thereof are shown in FIG. 3.

Measurement of Platelet Damage
1.0 μL anti-CD41a antibody APC label (Bio Legend 303710)
1.0 μL anti-CD42b antibody PE label (Bio Legend 303906)
5 μL Annexin V FITC label (BD Biosciences 556419)

Figure 3:
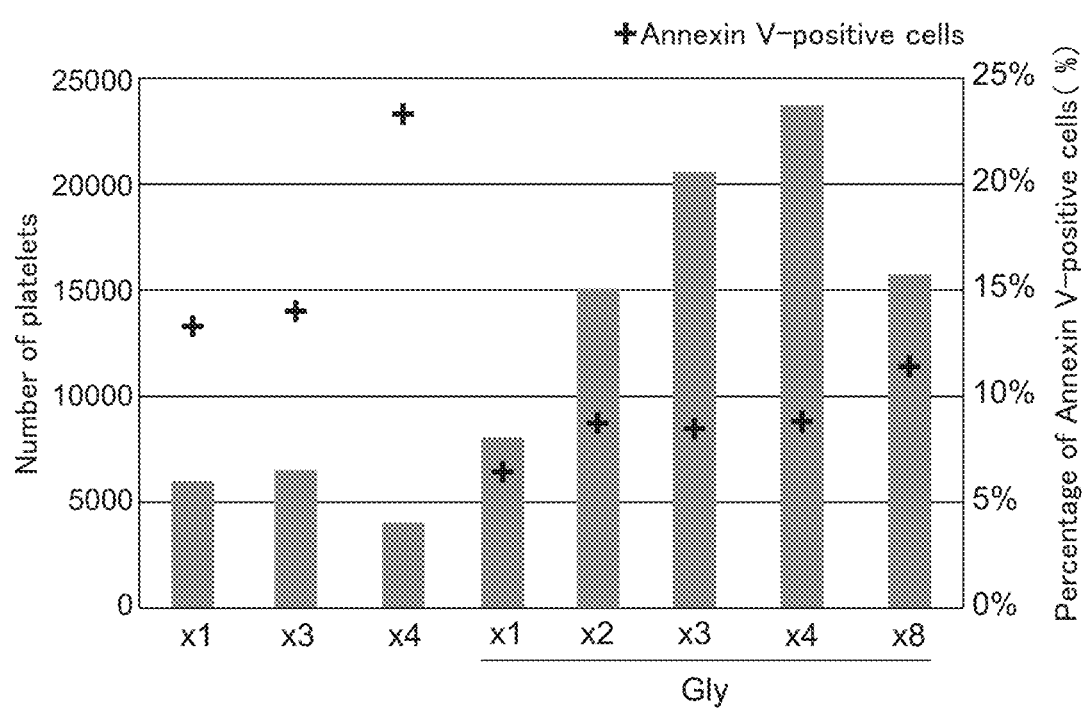
FIG. 3 is a graph showing the number of platelets and the percentage of Annexin V-positive cells in Example 1.

FIG. 3 is a graph showing the number of platelets and the percentage of Annexin V-positive cells. In FIG. 3, the horizontal axis indicates cell dissemination density and whether or not glycine is added, and the vertical axis indicates the number of platelets or the percentage of Annexin V-positive cells. As shown in FIG. 3, in controls, when the megakaryocyte dissemination density at the start of platelet production was increased, the percentage of Annexin V-positive cells was increased, i.e., platelets were deteriorated in the culture at a cell density three times the normal cell density, and platelets were deteriorated and the number of platelets were decreased in the culture at a cell density four times the normal cell density. In contrast, in the examples in which glycine was added, the deterioration of platelet was suppressed and the number of platelets was increased in the culture at any dissemination density as compared with the controls. A reduction in the percentage of deteriorated platelet means an increase in the percentage of functional platelet. Therefore, it has been found that, the ability of megakaryocyte to produce platelets can be improved and the bioactivity of platelets produced can be improved by adding glycine, and that these effects are particularly remarkable in the high-density culture.

Example 2

It was examined that the bioactivity of platelets produced can be improved by performing the high-density culture in the presence of cysteine.

The increase percentages of MFIs of CD62p and PAC-1 were calculated in the same manner as in Example 1(3) except that platelet was produced using a platelet production medium being added with cysteine at a predetermined concentration (1, 5, or 10 mmol/L) instead of glycine. The platelet production medium contains 0.6 to 0.8 mmol/L cysteine. Therefore, the concentration of the cysteine in the platelet production medium after being added with cysteine are about 2 to about 11 mmol/L. As a control, the increase percentage of MFIs of CD62p and PAC-1 was calculated in the same manner except that no cysteine was added. The results thereof are shown in FIG. 4.

Figure 4:
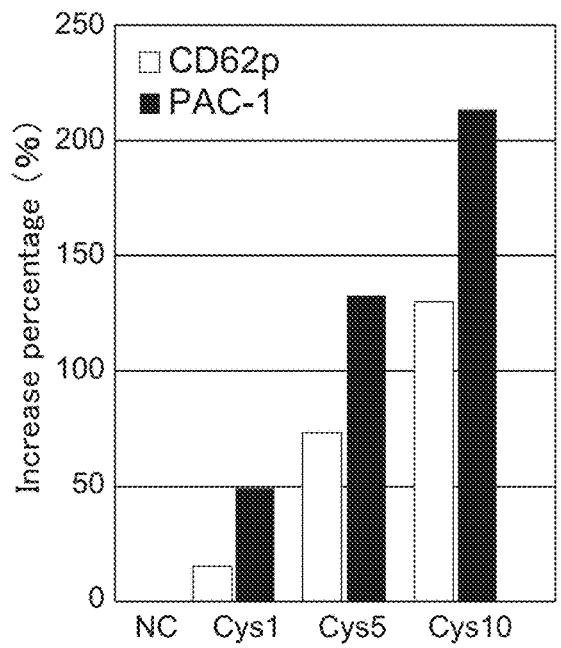
FIG. 4 is a graph showing the increase percentage of MFIs of CD62p and PAC-1 in Example 2.

FIG. 4 is a graph showing the increase percentage of MFIs of CD62p and PAC-1. In FIG. 4, the horizontal axis indicates the condition of cell dissemination density and cysteine concentration, and the vertical axis indicates the increase percentage of MFI. As shown in FIG. 4, the expression levels of CD62p and PAC-1 were increased at all cysteine concentrations compared to the control (NC) without being added with cysteine. In addition, the expression levels of CD62p and PAC-1 were increased in a concentration-dependent manner. From these results, it has been found that the bioactivity of platelets produced in high-density culture can be improved by adding cysteine.

Example 3

The decrease in the ability of megakaryocyte derived from different pluripotent cells to produce platelets in the high-density culture and the improvement in the ability of megakaryocyte to produce platelets by performing the high-density culture in the presence of glycine were examined.

(1) iPS Cells iPS cells were induced by introducing c-MYC, OCT3/4, SOX2, and KLF4 into immortalized megakaryocyte cell line (SeV2-MKCL) obtained in Example 1(1-6) by the Sendai virus vector according to the method described in WO 2010/134526. Next, immortalized megakaryocyte cell lines were induced in the same manner as in Examples 1(1-1) to (1-6) except that the induced iPS cells were used instead of the human iPS cells (TKDN SeV2). Further, as to the obtained immortalized megakaryocyte cell line, the number of platelets was counted and the platelet concentration was calculated in the same manner as in Example 1(2). Then, the P/M ratio was calculated based on the megakaryocyte cell density (dissemination density) at the start of production of platelets and the platelet concentration. As a control, the platelet concentration and the P/M ratio were calculated in the same manner except that the cell dissemination density was set to $1.0 \times 10^5$ cells/mL ($\times 1$) or $4.0 \times 10^5$ cells/mL ($\times 4$) and the glycine-non-added platelet production medium was used. The results are shown in FIGS. 5A and 5B.

Figures 5A, 5B:
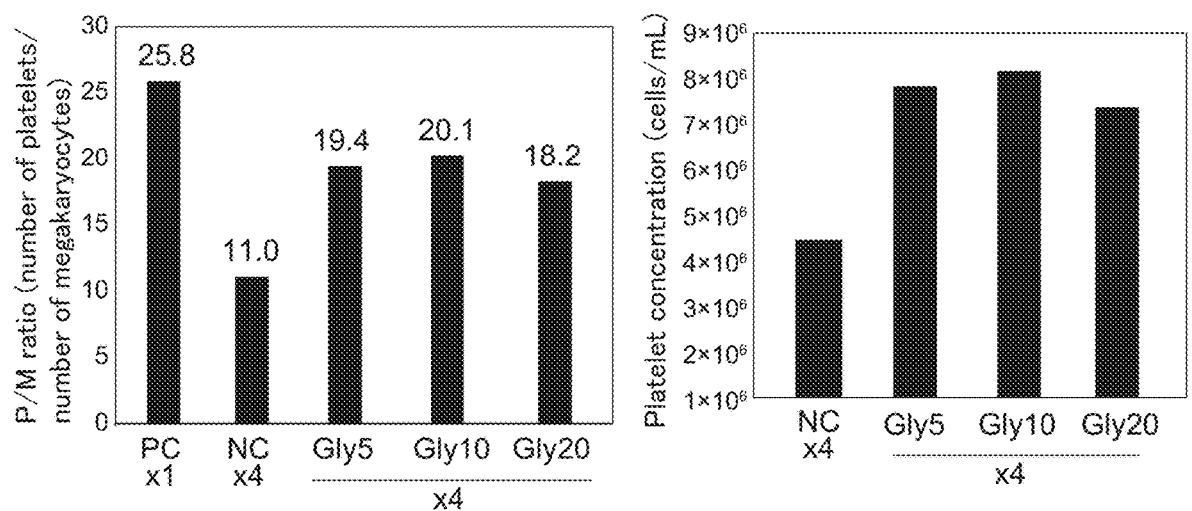
FIGS. 5A and 5B are graphs showing the ratio of the number of platelets to the number of megakaryocytes and the platelet concentration in Example 3, respectively.

FIGS. 5A and 5B are graphs each showing the P/M ratio and the platelet concentration. Each horizontal axis of FIGS. 5A and 5B indicates the condition of cell dissemination density and glycine concentration, the vertical axis of FIG. 5A indicates the P/M ratio, and the vertical axis of FIG. 5B indicates the platelet concentration. The numerals in FIG. 5A each indicate the P/M ratio. As shown in FIG. 5A, in the control without being added with glycine, the ability of megakaryocyte to produce platelets was decreased in the high-density culture ($\times 4$). In contrast, as shown in FIGS. 5A and 5B, when glycine was added, the ability of megakaryocyte to produce platelets was improved and the platelet concentration was increased at any glycine concentration as compared with the control in the high-density culture. From these results, it has been found that, by adding glycine, the ability of megakaryocyte to produce platelets in the high-density culture can be improved.

(2) iPS Cell Line

Immortalized megakaryocyte cell lines were induced in the same manner as in Examples 1(1-1) to (1-6) except that human iPS cells (NIH5 and NIH8) were used instead of the human iPS cells (TKDN SeV2). As to the obtained immortalized megakaryocyte cell line, the number of platelets was counted and the platelet concentration was calculated in the same manner as in Example 1(2) except that the cell dissemination density was set to $4.0 \times 10^5$ cells/mL ($\times 4$) or $6.0 \times 10^5$ cells/mL ($\times 6$) and the culture was performed for 5 days. As a control, the platelet concentration was calculated in the same manner except that the cell dissemination density was set to $1.0 \times 10^5$ cells/mL ($\times 1$), $4.0 \times 10^5$ cells/mL ($\times 4$), or $6.0 \times 10^5$ cells/mL ($\times 6$), and the glycine-non-added platelet production medium was used. The results are shown in FIGS. 6A and 6B.

Figure 6A:
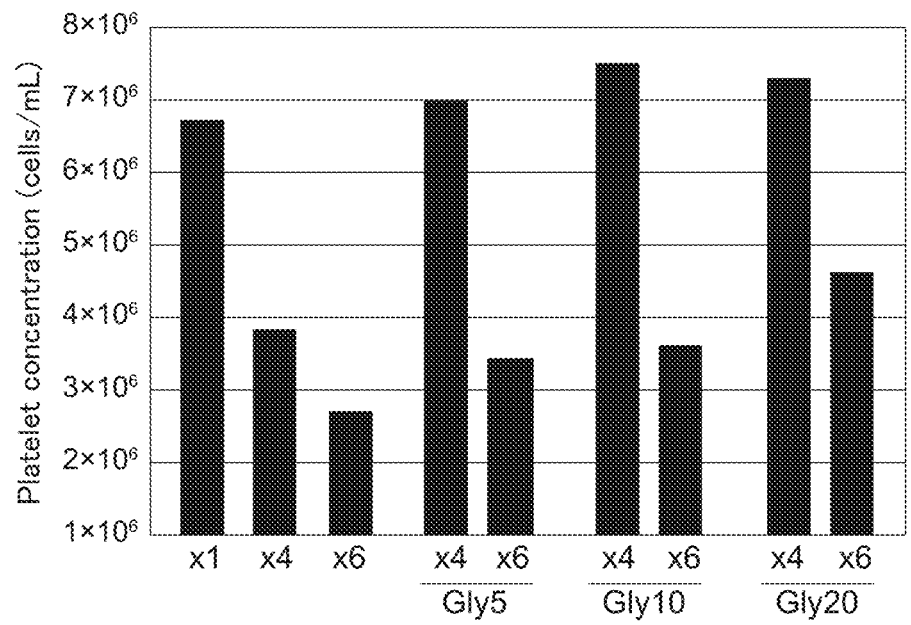
FIGS. 6A and 6B are graphs each showing the platelet concentration in Example 3.
Figure 6B:
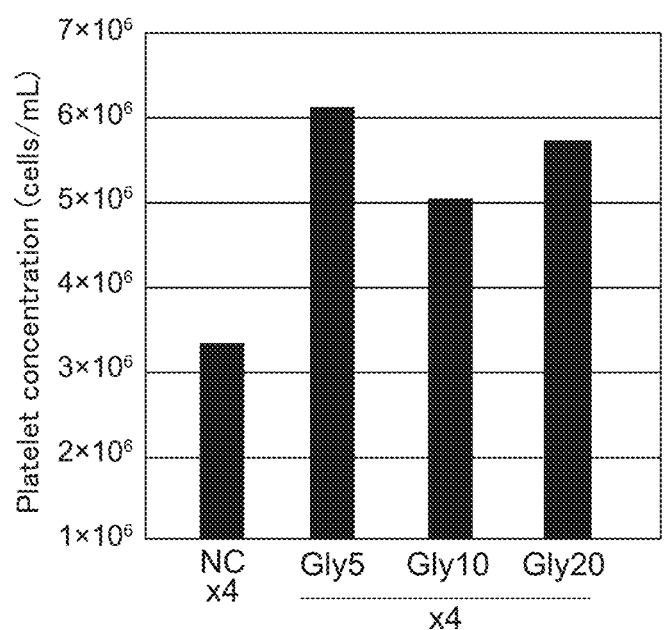

FIGS. 6A and 6B are graphs each showing the platelet concentration. FIG. 6A shows the result of NIH5, and FIG. 6B shows the result of NIH8. In FIGS. 6A and 6B, the horizontal axis indicates the condition of cell dissemination density and glycine concentration, and the vertical axis indicates the platelet concentration. As shown in FIGS. 6A and 6B, the platelet concentration was increased at any dissemination density as compared with the control in the high-density culture. From these results, it has been found that, by adding glycine, the ability of megakaryocyte to produce platelets in the high-density culture can be improved.

From the above, as to megakaryocytes derived from different cells, it has been found that, according to the production method of the present invention, the ability of megakaryocyte to produce platelets is decreased in the high-density culture and the ability of megakaryocyte to produce platelets can be improved by performing the high-density culture in the presence of glycine.

While the present invention has been described above with reference to illustrative example embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2017-179137 filed on Sep. 19, 2017. The entire subject matter of the Japanese Patent Application is incorporated herein by reference.

INDUSTRIAL APPLICABILITY

As described above, according to the present invention, for example, at least one of the ability of megakaryocyte to produce platelets and the bioactivity of platelets produced can be improved in the high-density culture, so that at least one of the efficient (high yield) production of platelets and the production of highly functional platelets can be achieved in the high-density culture. Therefore, the present invention is extremely useful, for example, in the cellular medicine field and medical field in which platelets are used.

The invention claimed is:

1. A method for producing platelets comprising:
culturing megakaryocytes in the presence of glycine at 2 to 21 mmol/L to produce platelets from the megakaryocytes,
wherein
the platelet-producing ability of the megakaryocytes is improved compared with megakaryocytes cultured in a medium in which the concentration of the glycine is lower than 2 mmol/L.

2. The method for producing platelets according to claim 1, wherein the concentration of the glycine is 6 to 21 mmol/L.

3. The method for producing platelets according to claim 1, wherein the concentration of the glycine is 11 to 21 mmol/L.

4. The method for producing platelets according to claim 1, wherein the culturing megakaryocytes is performed in the presence of cysteine at 2 to 11 mmol/L, in addition to the glycine.

5. The method for producing platelets according to claim 1, wherein a megakaryocyte cell density at a start of production of the platelets is $3 \times 10^5$ cells/mL or more.

6. The method for producing platelets according to claim 1, wherein the megakaryocyte is an immortalized megakaryocyte.

7. The method for producing platelets according to claim 1, wherein the megakaryocyte is derived from pluripotent cells.

8. The method for producing platelets according to claim 7, wherein the pluripotent cell is an induced pluripotent stem cell.

9. The method for producing platelets according to claim 1, wherein the megakaryocyte is of human origin.

10. A method for producing a platelet product, comprising:
culturing megakaryocytes in the presence of glycine at 2 to 21 mmol/L to produce platelets from the megakaryocytes; and
producing a platelet product from the platelets,
wherein
the platelet-producing ability of the megakaryocytes is improved compared with megakaryocytes cultured in a medium in which the concentration of the glycine is lower than 2 mmol/L.

11. A method for producing a blood product, comprising:
culturing megakaryocytes in the presence of glycine at 2 to 21 mmol/L to produce platelets from the megakaryocytes; and
producing a blood product by mixing the platelets and other components,
wherein
the platelet-producing ability of the megakaryocytes is improved compared with megakaryocytes cultured in a medium in which the concentration of the glycine is lower than 2 mmol/L.

12. The method for producing platelets according to claim 1, wherein a megakaryocyte cell density at a start of production of the platelets is $1 \times 10^5$ cells/mL or more.

13. The method for producing a platelet product according to claim 10, wherein the culturing megakaryocytes is performed in the presence of cysteine at 2 to 11 mmol/L, in addition to the glycine.

14. The method for producing a blood product according to claim 11, wherein the culturing megakaryocytes is performed in the presence of cysteine at 2 to 11 mmol/L, in addition to the glycine.

15. A method for producing platelets comprising:
culturing megakaryocytes in the presence of cysteine at 2 to 11 mmol/L to produce platelets from the megakaryocytes,
wherein the platelet-producing ability of the megakaryocytes is improved compared with megakaryocytes cultured in a medium in which the concentration of the cysteine is lower than 2 mmol/L.

16. The method for producing platelets according to claim 15, wherein a megakaryocyte cell density at a start of production of the platelets is $3 \times 10^5$ cells/mL or more.

17. The method for producing platelets according to claim 15, wherein the megakaryocyte is an immortalized megakaryocyte.

18. The method for producing platelets according to claim 15, wherein the megakaryocyte is derived from pluripotent cells.

19. A method for producing a platelet product, comprising:
culturing megakaryocytes in the presence of cysteine at 2 to 11 mmol/L to produce platelets from the megakaryocytes; and
producing a platelet product from the platelets,
wherein the platelet-producing ability of the megakaryocytes is improved compared with megakaryocytes cultured in a medium in which the concentration of the cysteine is lower than 2 mmol/L.

20. A method for producing a blood product, comprising:
culturing megakaryocytes in the presence of cysteine at 2 to 11 mmol/L to produce platelets from the megakaryocytes; and
producing a platelet product from the platelets,
wherein the platelet-producing ability of the megakaryocytes is improved compared with megakaryocytes cultured in a medium in which the concentration of the cysteine is lower than 2 mmol/L.

* * * * *